United States Patent [19]

Puckette

[11] Patent Number: 4,845,306
[45] Date of Patent: Jul. 4, 1989

[54] CATALYST MATERIAL RECOVERY OR CONCENTRATION PROCESS

[75] Inventor: Thomas A. Puckette, Longview, Tex.

[73] Assignee: Eastman Kodak Company, Rochester, N.Y.

[21] Appl. No.: 218,017

[22] Filed: Jul. 12, 1988

Related U.S. Application Data

[63] Continuation-in-part of Ser. No. 41,969, Apr. 24, 1987.

[51] Int. Cl.⁴ .......................... C07C 45/50; C07F 9/02
[52] U.S. Cl. ...................................... 568/454; 556/21; 556/22; 556/136; 568/492; 568/17
[58] Field of Search ................... 568/454, 492; 556/21, 556/22, 136

[56] References Cited

U.S. PATENT DOCUMENTS 2,658,069  11/1953  van der Waal .................. 568/492
4,678,857  7/1987  Dureanleau et al. ............. 568/492

FOREIGN PATENT DOCUMENTS 2833469  2/1980  Fed. Rep. of Germany ...... 568/492
035314  4/1974  Japan ................................. 568/492
1238751  10/1986  Japan ................................. 568/492

Primary Examiner—Werren B. Lone
Attorney, Agent, or Firm—S. E. Reiter; William P. Heath, Jr.; Thomas R. Savitsky

[57] ABSTRACT

Disclosed is a process for recovering or concentrating active catalyst materials from a substantially homogeneous system comprising:
(a) active catalyst materials which comprise
  (i) triorganophosphine-rhodium complexes, and
  (ii) free triorganophosphine;
(b) oxidized triorganophosphine residues,
(c) iron carboxylate salts,
(d) pump oils, and
(e) aldehydes and aldol condensation products thereof;
said processing comprising:
(1) admixing a portion of said homogeneous system with about 1 up to 100 volumes (relative to the volume of said portion) of at least one nonpolar hydrophobic hydrocarbon diluent selected from the group consisting of saturated or unsaturated aliphatic hydrocarbon having in the range of 3 up to 20 carbon atoms and aromatic or hydrocarbyl-substituted aromatic hydrocarbons having in the range of 6 up to 22 carbon atoms to produce a diluted homogeneous system,
(2) contacting said diluted homogeneous system with 0.1 up to 20 volumes (relative to the volume of said nonpolar hydrophobic solvent) of at least one aqueous polar hydrophilic organic solvent selected from the group consisting of:
  aliphatic carboxylic acids having in the range of 1 up to 3 carbon atoms,
  aliphatic alcohols having in the range of 1 up to 3 carbon atoms,
  acetonitrile,
  acetone,
  dimethylformamide,
  dimethylacetamide,
  methyl ethyl ketone,
  1,4-dioxane,
  polyols having in the range of 2 up to 6 carbon atoms,
  glycol ethers having in the range of 4 up to 12 carbon atoms,
  as well as mixtures of any two or more thereof, and allowing the nonpolar hydrophobic hydrocarbon solvent and the aqueous polar hydrophilic organic solvent to separate into layers, and thereafter
(3) separating the hydrocarbon layer from the aqueous polar hydrophilic organic layer.

18 Claims, No Drawings

CATALYST MATERIAL RECOVERY OR CONCENTRATION PROCESS

This application is a continuation-in-part of application Ser. No. 41,969, filed Apr. 24, 1987, now copending; which application is incorporated by reference in its entirety.

FIELD OF THE INVENTION

The present invention concerns a process for recovering or concentrating catalyst material from a chemical operation, wherein the active catalyst material is preferentially soluble in nonpolar hydrophobic solvents while the spent or inactive catalyst material is preferentially soluble in polar hydrophilic solvents.

BACKGROUND OF THE INVENTION

The present invention is concerned with the recovery of metal values from a variety of chemical operations, e.g., hydroformylation operations employing expensive catalyst metals such as rhodium or cobalt. In addition, the present invention relates to the recovery of metal values from chemical operations employing such metals as platinum, palladium, nickel, or iridium, or other metals complexed with triorganophosphine ligand(s). The gradual oxidation of the triorganophosphine ligand(s) to phosphine oxide(s) which is (are) catalytically inactive material(s), eventually results in levels of such material(s) in the catalyst system or solution as to exert a negative effect on the desired chemical operation.

With particular respect to hydroformylation reactions, the gradual accumulation of high boiling materials such as aldol condensation by-products is inevitable. Excess quantities of such materials must be removed in order to maintain the proper volume or level of the active catalyst system. Moreover, the gradual accumulation of contaminants such as iron salts and pump oils (polyglycol oils) can cause adverse changes in catalyst selectivity, reaction rate, and by-product production.

In addition, hydroformylation operations typically require the addition of make-up triorganophosphine ligand to compensate for ligand which is oxidized to phosphine oxide. Thus, not only does such oxidation effect an additional by-product build-up but also creates a significant financial burden, particularly when the ligand is a costly phosphine derivative.

The removal of these by-products and contaminants is frequently difficult due to the complexity of the catalyst system. The catalyst system contains valuable unassociated triorganophosphine ligand(s) and the active catalyst material such as rhodium complexed with ligand, as well as the by-product contaminants. The loss of substantial amounts of the catalyst metal, in particular, rhodium, in heretofore proposed catalyst system purification procedures has either prevented their commercial adoption altogether or has limited their desirability for use.

A procedure for extracting catalyst metals such as rhodium from hydroformylation operations reported in British Pat. No. 1,502,339 by Tampieri et al. However, the efficiency of the Tampieri process is low and, therefore, not commercially attractive. Tampieri describes a process for the removal of triphenylphosphine oxide from a hydroformylation catalyst system whereby the catalyst system is heated (distilled) to remove the aldehyde product and other volatiles. The residue from the distillation is typically composed of aldol condensation products (15 percent), triphenylphosphine plus triphenylphosphine-rhodium complex (65 percent) and triphenylphosphine oxide (20 percent). This residue is washed with an aqueous solution of methanol, acetone, acetonitrile, or dimethylformamide to give a suspension which separates upon standing at 75 degrees C. This procedure is alleged to remove up to 45 percent of the triphenylphosphine oxide along with about 2.5 percent of the triphenylphosphine-rhodium complex. The phosphine-rhodium complex is recovered by back-washing (extracting) the aqueous medium with a hydrocarbon solvent such as hexane or toluene which extract is concentrated and returned along with the original catalyst to the reactor.

OBJECT OF THE INVENTION

It is, therefore, an object of the present invention to provide a commercially practical process for the selective removal of heavy reaction by-products, contaminants, and spent catalyst materials, e.g., phosphine oxides, from catalyst systems with negligible catalyst metal loss and without significant loss of catalytic activity; and to provide for the selective recovery of valuable triorganophosphine oxide which can be converted to active ligand species by selective reduction in known manner.

Another object of the present invention is to provide a markedly improved process for concentrating catalyst materials without the need for the plurality of steps and complex procedure such as disclosed by Tampieri.

These and other objects of the invention will become apparent upon inspection of the following description and appended claims.

SUMMARY OF THE INVENTION

These and other objects of the present invention have been attained by a process wherein the active catalyst materials of a substantially homogeneous catalyst system are concentrated and/or recovered by first contacting at least a portion of such catalyst system with a nonpolar hydrocarbon diluent, then contacting the diluent-containing catalyst system with an aqueous polar hydrophilic organic extractant, and finally allowing the diluent and extractant portions to form into layers. Concentrated active catalyst materials can then be recovered from the diluent layer.

The present invention represents an improvement over the art in that the efficiency of phosphine oxide extraction from the catalyst system can be increased, and catalyst losses as a result of such extraction are reduced by diluting the catalyst system with an appropriate hydrocarbon diluent prior to the extraction of undesirable polar materials with aqueous, polar, hydrophilic solvent. The extraction of phosphine oxide is thus increased to 60 to 80 percent of the original amount present, while the catalyst losses are reduced, compared to results obtained when extraction is carried out without using the hydrocarbon diluent. The process of the present invention thus obviates the need for additional extraction.

Moreover, the addition of hydrocarbon diluent to the catalyst system is a further improvement over the art in that it causes polar contaminants such as soluble iron carboxylates to precipitate, and pump oils to separate from the catalyst-containing layer upon contacting with the aqueous, polar, hydrophilic solvent extractant. The carboxylate materials are removed by filtration of the mixture and the pump oils separate into the extractant.

Addition of hydrocarbon diluent also aids in promoting the separation of the organic (catalyst-containing) and aqueous (polar impurity-containing) layers, thereby facilitating the recovery of catalyst. In contrast, the prior art process disclosed by Tampieri describes the mixture from his extraction step as a suspension. Such a suspension has been found to be slow to separate into phases and the two phases are difficult to separate cleanly. In contrast, the addition of the diluent according to the present invention provides a mixture from which the layers separate rapidly and cleanly, allowing for rapid processing of the catalyst system for recovery of active catalyst therefrom.

The process of the present invention is quite flexible as it is capable of working with catalyst systems which contain anywhere from very low up to very high levels of the phosphorus components. The extraction and separation of the organic and aqueous layers can conveniently be carried out at room temperature as the invention process does not require the use of elevated temperatures.

The process of the present invention particularly well suited for use with hydroformylation catalysts which contain low levels of phosphorus compounds and high levels of aldol condensation products and aldehydes. In addition, the process of the present invention is very flexible and works for a wide variety of phosphines and phosphine oxides providing they meet the requirements that the phosphine and phosphine-precious metal complex be highly soluble in a hydrocarbon phase, yet relatively insoluble in the aqueous organic extractant phase, and that the phosphine oxide be preferentially soluble in the aqueous organic extractant phase.

The process of the present invention can be used not only for concentration and purification of active catalyst material, but also to control the accumulation of heavy by-products in a reaction catalyst provided that the catalytically active species is nonpolar and hydrocarbon soluble while the materials to be removed are moderately polar and soluble in aqueous organic solvents. The process is not limited to use in hydroformylation operations, and can be used in any system in which the catalyst and contaminants meet the solubility requirements.

The invention has general utility for isolating the oxidation products of phosphine ligands from the catalyst liquid. Triorganophosphine ligands, for example, are an important part of many catalytic reaction catalysts and the replacement of ligand which has been lost due to oxidation can be expensive, especially if the ligand contains unusual organic groups or chirality. This process also allows for the isolation of the phosphine oxide from the catalyst ligand so that it could potentially be recycled to the phosphine. For example, the process would have application in the recovery of chiral phosphines used in asymmetric hydrogenation reactions.

DETAILED DESCRIPTION OF THE INVENTION

In accordance with the present invention, there is provided a process for recovering or concentrating active catalyst materials from a substantially homogeneous system comprising:
(a) active catalyst materials which comprise
  (i) triorganophosphine-rhodium complexes, and
  (ii) free triorganophosphine;
(b) oxidized triorganophosphine residues,
(c) iron carboxylate salts,
(d) pump oils, and
(e) aldehydes and aldol condensation products thereof; said processing comprising:
(1) admixing a portion of said homogeneous system with about 1 up to 100 volumes (relative to the volume of said portion) of at least one nonpolar hydrophobic hydrocarbon diluent selected from the group consisting of saturated or unsaturated aliphatic hydrocarbon having in the range of 3 up to 20 carbon atoms and aromatic or hydrocarbyl-substituted aromatic hydrocarbons having in the range of 6 up to 22 carbon atoms to produce a diluted homogeneous system,
(2) contacting said diluted homogeneous system with 0.1 up to 20 volumes (relative to the volume of said nonpolar hydrophobic solvent) of at least one aqueous polar hydrophilic organic solvent selected from the group consisting of:
  aliphatic carboxylic acids having in the range of 1 up to 3 carbon atoms,
  aliphatic alcohols having in the range of 1 up to 3 carbon atoms,
  acetonitrile,
  acetone,
  dimethylformamide,
  dimethylacetamide,
  methyl ethyl ketone,
  1,4-dioxane,
  polyols having in the range of 2 up to 6 carbon atoms,
  glycol ethers having in the range of 4 up to 12 carbon atoms,
  as well as mixtures of any two or more thereof, and allowing the nonpolar hydrophobic hydrocarbon solvent and the aqueous polar hydrophilic organic solvent to separate into layers, and thereafter
(3) separating the hydrocarbon layer from the aqueous polar hydrophilic organic layer.

Organophosphine materials to which the present invention is applicable are triorganophosphines which have the formula $P(R)_3$ or bidentate phosphorus moieties having the formula $PR_2\text{-}L\text{-}PR_2$ wherein each R radical is independently a hydrocarbyl moiety having from 1 up to 20 carbon atoms, wherein each of these radicals can optionally be substituted with 1-3 hydrocarbyl radicals, wherein any of the above hydrocarbyl radicals is optionally substituted with 1-3 groups selected from alkoxy, aryloxy, cycloalkoxy, carboxyesters, carboxy, alkanoyl, aroyl, hydroxy, alkoxyalkoxy, alkoxyalkyl, or acyloxy, and wherein any of the above aryl radicals can optionally be substituted with 1-3 of the above groups or halogen or cyano; and wherein L is an alkylene, alkenylene, arylene moiety having in the range of 1-20 carbon atoms, optionally substituted as is described for R.

In all of the radicals, moieties or groups of the organophosphine material, the alkyl moieties are straight or branched chain of 1-20 carbons, preferably 1-6 carbons, the aryl moieties have in the range of 6-14 carbons, preferably 6 carbons, and the cycloalkyl moieties have in the range of 4-8 carbons, preferably 6 carbons.

Exemplary organophosphine materials which can be recovered and/or concentrated by the process of the present invention include triphenylphosphine, tribenzylphosphine, tricyclohexylphosphine, diphenylcyclohexylphosphine, 2,2'-bis(diphenylphosphinomethyl)-1,1'-biphenyl, tri-n-butylphosphine, tri-n-octylphosphine, alpha, beta'-bis(diphenylphosphino)-2-ethyltoluene, -2-ethyltoluene, 1,2-bis[2-(diphenylphosphino)ethyl]benzene, and the like.

Typical catalyst systems employed in the practice of the present invention comprise triorganophosphine-rhodium complexes which, during the hydroformylation reaction (for which reaction such materials are particularly useful), are also usually complexed with carbon monoxide.

A typical chemical process to which the present invention is applicable is a hydroformylation reaction which can be carried out, for example, in a gas sparged reactor such that the catalyst does not leave the reaction zone with the aldehyde product which is taken overhead by the unreacted gases such as propylene, hydrogen and carbon monoxide. The overhead gases are then chilled in a vapor liquid separator to condense out the aldehyde product, the unreacted gases being recycled to the reactor and the liquid product let down to atmospheric pressure for separation and purification by conventional techniques. A continuous or periodic side draw from the reactor is the preferable means for obtaining a portion of the catalyst system for treatment in accordance with the present invention. The treated catalyst is then continuously or periodically returned to the reactor typically after the addition of make-up ligand thereto.

The metal catalyst components are initially charged preferably with solvent to the reactor through suitable pressurized pumping means, typically in their soluble forms, e.g., their carboxylate salts or mineral acid salts or the like well known to the art as disclosed, for example, in U.S. Pat. No. 2,880,241. Charged therewith or separately is one or more of the organophosphine materials in amounts such that the molar ratio of organophosphine to catalyst metal, e.g. rhodium, in the reactor is maintained at from about 1.0 to about 200 or more, preferably from about 2.0 to about 10.0, and most preferably from about 2.3 to about 4.0.

The operation under typical steady - state conditions is maintained as follows:

(A) pressures from about 50 to about 800 psig are operable, with from about 100 to about 400 psig being preferred. The reaction temperatures can vary from about 20° to about 250° C., but preferably from about 50° to about 175° C. and most preferably from about 80° to about 150° C.;

(B) the syn gas is introduced into the reactor in a continuous manner by means, for example, of a primary compressor, and the ratio of hydrogen to carbon monoxide in the feed may be selected according to the particular olefin being hydroformylated and the reaction conditions present, as is well known in the art. Generally, the molar ratio of hydrogen to carbon monoxide in the reactor is maintained within the range of about 0.5 to about 4.0, but it has been found in many hydroformylations that the rate of reaction as well as yield of the desired product may be increased by increasing the hydrogen to carbon monoxide molar ratio above 4.0, and up to about 10.0 or more. The syn gas preferably is present in a molar excess (total moles of $H_2+CO$) with respect to the olefin and the molar ratio varies typically from about 0.5 to about 20, preferably from about 1.2 to about 6;

(C) the olefin is fed to the reactor by means of suitable pumps capable of operating under substantial pressures and the feed rates of the olefin and syn gas are selected to maintain the above-recited molar ratios of these reactants in the reactor. Typical olefins to which the present invention is applicable include straight or branched chain α-olefins containing from 2 to 20 carbon atoms and preferably from 2 to 10 carbon atoms, and optionally containing groups or substituents which do not interfere with the hydroformylation process. Illustrative such α-olefins are ethylene, propylene, 1-butene, 2-methylpropylene, 2-methyl-1-butene, 1-pentene, 1-hexene, 1-heptene, 1-octene, 2-ethyl-1-hexene, 1-dodecene and 1-octadecene. Also useful with the present invention are the internal olefins such as butene-2 and cyclic olefins such as cyclooctene. If desired, mixtures of olefins, particularly ethylene and propylene, can be fed to the reactor;

(D) any suitable solvent which does not adversely affect the hydroformylation process and which is inert with respect to the catalyst, olefin feed, syn gas and the hydroformylation products may be used in the operation. Inert solvents of this nature are well known to those skilled in the art and include benzene, xylene, toluene and their substituted derivatives, pentanes, naphtha, kerosene, mineral oils, cyclohexane, cyclopentane, ethers, esters, etheresters, alcohols, acetals, ketones, and various mixtures thereof. Preferred solvents are those which are sufficiently high boiling to remain for the most part in the gas sparged reactor, and include 2,2,4-trimethyl-1,3-pentanediol monoisobutyrate, and its isomers, and the by-products such as alcohols, esters, acetals, and hydroxyaldehydes produced in the hydroformylation reaction and retained as high boiling liquids at the bottom of the subsequent distillation columns. Maintenance of proper levels of these solvents is achieved through distillation of the aforementioned side draw from the reaction vessel in known manner; and (E) the hydroformylation can be carried out with very small amounts of catalyst containing from about $1 \times 10^{-6}$ moles of rhodium (calculated as Rh°) per mole of olefin in the reaction zone. However, such low catalyst concentrations are not commercially desirable since the reaction rates are low. The upper catalyst concentration is essentially unlimited and appears to be dictated principally by the high cost of rhodium and the fact that no advantage is evident in the use of catalyst containing above about $1 \times 10^{-1}$ moles of rhodium per mole of olefin. A concentration of from about $1 \times 10^{-5}$ moles to about $5 \times 10^{-2}$ moles of rhodium per mole of olefin is preferred, and from about $1 \times 10^{-4}$ to about $1 \times 10^{-2}$ is most preferred.

The recovery and/or concentration process of the present invention is preferably carried out under an inert, oxygen free atmosphere, typically as follows.

Volume reduction may optionally be employed to reduce the volume of the catalyst system portion subjected to the recovery and/or concentration process of the present invention. Preferably such reduction is accomplished under vacuum to eliminate olefin and reactive aldehydes and to provide a more readily manageable catalyst system concentrate for further treatment. This crude concentration is best done at high vacuum in a wiped film evaporator, rotary evaporator, simple distillation equipment or other suitable equipment. The resulting crude concentrate should be handled under a protective inert atmosphere such as nitrogen to prevent the oxidation of phosphine ligand which may be present therein.

In a typical run, the catalyst system portion is reduced to about ½ to about 1/25 of its original volume.

When this crude concentration step is not used, aldehydes and other volatiles may further react to form additional quantities of reaction by-products, and the overall volume of material which must be handled may be unwieldly.

The dilution of the crude concentrate is carried out with a nonpolar, hydrophobic, hydrocarbon diluent.

Hydrocarbon diluents contemplated for use in the practice of the present invention include saturated and unsaturated aliphatic hydrocarbons having in the range of 3 up to 20 carbon atoms and aromatic or hydrocarbyl-substituted aromatic hydrocarbons having in the range of 6 up to 22 carbon atoms. Exemplary hydrocarbon diluents include propane, propylene, butane, butene, pentane, pentene, hexane, hexene, heptane, heptene, octane, octene, kerosene, mineral spirits, petroleum ethers, and the like, as well as mixtures of any two or more thereof.

The volumetric ratio of diluent to the catalyst system portion, neat or crude concentrated, can be widely varied, for example, from about 0.5 to about 100, preferably from about 1 to about 10, and most preferably from about 3 to about 7.

The dilution reduces the viscosity of this concentrate, resulting in solutions which are easier to mix and manipulate, and also reduces the solubility of polar contaminants such as iron salts and polyglycol pump fluids. The dilution also serves to reduce the solubility of polar by-products such as aldol condensation products and triorganophosphine oxides. This dilution also should be conducted under an inert atmosphere.

The dilute catalyst system portion, either neat or as a concentrate, is then washed with an aqueous polar hydrophilic organic extractant. The aqueous organic extractant comprises an appropriate mixture of water and an organic solvent containing sufficient quantities of water so as to obtain phase separation (between the polar, organic phase and the nonpolar hydrocarbon phase), yet not so much water as to prevent the solubilization of the polar catalyst system components in the organic phase. Typically, the amount of water in the aqueous extractant will fall in the range of about 10 up to 65 vol % of the extractant.

The polar organic solvent employed for the extraction can be varied greatly, and include, but are not limited to, acetonitrile, acetone, dimethylformamide, dimethylacetamide, methyl ethyl ketone, 1,4-dioxane, aliphatic alcohols having in the range of 1 to 3 carbon atoms, aliphatic carboxylic acids having in the range of 1 to 3 carbon, atoms, polyols having in the range of 2 to 6 carbon atoms, glycol ethers having in the range of 4 to 12 carbon atoms, and the like, as well as mixtures of any two or more thereof. In general, any water soluble solvent which will form a hydrocarbon insoluble mixture may be used. Preference is given to more volatile organic solvents as this facilitates solvent and catalyst recovery.

In a typical application, the diluted catalyst system portion, either neat or as a concentrate, is washed with in the range of about 0.1 up to 20 volumes (relative to the volume of diluent) of aqueous organic medium; with volumetric ratios in the range of 0.5 up to 5 preferred and ratios in the range of 0.8 up to 1.5 being most preferred. A presently preferred extraction is carried out with an equal volume of a methanol-water (80/20, vol/vol) mixture.

The level of the organic solvent in the aqueous extractant is important in achieving optimum results. For the specific case of methanol, the MeOH content preferably should be in the range of 70 to 85 percent of the extractant. If the level falls below about 70 percent, the extraction of phosphine oxides and polar contaminants drops off as these materials are substantially insoluble in water. If the level exceeds about 85 percent, the water insoluble rhodium complexes begin to extract. For the case of acetonitrile-water mixtures, the extractant preferably should contain 35 to 50 percent acetonitrile. With acetone as the organic solvent, the extractant preferably should contain 30 to 55 percent acetone. It is within the purview of one skilled in the art to determine the most effective concentration of a particular extractant solvent.

The washing may be done by stirring the solutions together for about 2 to about 16 hours or by refluxing and stirring the solutions for about 0.5 to about 2 hours. These conditions will greatly enhance removal of iron salts which precipitate from the solution at this point as a finely divided solid. The precipitation will be incomplete if short mixing times at low temperatures are used. The shorter mixing time at reflux is the preferred procedure in that the refluxing extraction yields the iron salts more readily as granular solids which can be easily filtered. Iron chelating agents can be added to the extracting layers to aid the precipitation of the iron, but in general such agents are not required to effect its removal.

In a typical catalyst recovery and/or concentration according to this invention wherein the catalyst system contains polar materials such as iron salts, a layer of solids may form at the interface between the hydrocarbon layer and the aqueous organic extractant. The solids include abrasive materials from the reactor system such as fines from bearings and precipitated iron compounds. The mixture of the two liquid layers optionally can be filtered to remove the solids and then the layers are separated. The filtration may be carried out with any conventional filtration material such as filter paper or glass frit, but preferrably on diatomaceous earth or similar porous, high surface area material, to aid in removal of even fine particulate material.

After the optional filtration step, the hydrocarbon and aqueous organic layers are separated to give two independent homogeneous solvent systems. The upper layer is the hydrocarbon layer which contains substantially all of the concentrated metal catalyst in the form of organophosphine complexes, and also from about 45 to about 65 percent of the heavy by-products, the percentage depending on the nature of the by-products and the extracting solution. In the particular application employing 80 percent aqueous methanol, the hydrocarbon layer will contain from about 20 to about 30 percent of the organophosphine oxide with the remainder being present in the methanol-water layer.

As an optional final step of the present process, the catalyst can be returned to the reactor system. Optionally, the hydrocarbon diluent can be removed prior to this recycle of recovered catalyst, e.g., under reduced pressure to give a purified catalyst concentrate. This concentration step can frequently be eliminated, especially where the hydrocarbon diluent employed can also serve as a diluent or reactant in the desired reaction to which the catalyst is being returned. This concentrate can be charged directly to the reactor or can be diluted with an appropriate solvent such as product aldehyde, and then added to the reaction system in known manner.

This invention will be illustrated further by the following examples although it will be understood that these examples do not limit the invention and are for purposes of illustration only.

EXAMPLES

All procedures were carried out under an inert, oxygen-free atmosphere. All solvents were degassed prior to use. 1-Hexene and 1-octene were passed through a bed of silica gel to remove peroxide impurities prior to use.

Rhodium analyses were carried out by atomic absorption. Organophosphine content was determined by titration and gas chromatography and phosphine oxide content was determined by gas chromatography.

EXAMPLE 1

Preparation Of Rhodium 2-Ethylhexanoate Solution In Texanol® Solvent Used In Catalyst Feed The apparatus consists of a 5-liter three-necked flask equipped with a heating mantle, Teflon bladed mechanical stirrer, reflux condenser, and a thermometer. Sodium hydroxide (80 grams) was dissolved in 1,000 mL of water in the flask. 2-Ethylhexanoic acid (196 grams) was added to the flask and dissolved. Rhodium chloride hydrate (46.62 grams containing 20 grams of rhodium metal value) was dissolved in 900 mL of water separately and then added to the stirred sodium 2-ethylhexanoate solution in the flask. The mixture was heated to 95° C. and kept vigorously stirred for 1.5 hours. A dark green oil of crude product separated. The mixture was cooled to room temperature and 400 mL of Texanol (2,2,4-trimethylpentane -1,3-diol-monoisobutyrate) solvent was added with stirring. The two phases were separated. The aqueous layer was reextracted with three 400 mL Texanol washes which were combined with the first organic extract. The combined organic phases were washed with 1,000 mL of water. The water wash was combined with the original water wash for rhodium analysis. The combined organic phases were filtered through a 0.5-inch thick bed of celite and made up to 2 liters volume with Texanol solvent that was washed through the celite. The concentration of rhodium in the organic phase was 10,000 ppm and in the combined aqueous phase was 2 ppm.

EXAMPLE 2

Typical Bench-Scale Low Pressure Hydroformylation of Propylene Using Rhodium/-Tricyclohexyl -Tricyclohexyl Phosphine Catalyst The reactor consists of a vertically held stainless steel 4 foot by 1 inch (inside diameter) tube having a stainless steel filter element welded into its side near the bottom. The bottom of the tube has a drain valve and the top has a side port through which the vaporized products and unreacted gases leave the reactor. The top end of the tube is provided with a screwed plug which can be removed for charging the catalyst and which contains a thermowell whereby the temperature of the catalyst solution (reaction medium) in the reactor is measured accurately. Hydrogen and carbon monoxide are fed to the reactor from cylinders via pressure regulators and flow controllers which use differential pressure cells and air actuated flow control valves to maintain accurate flow. A third feed of nitrogen from a cylinder goes to the reactor via a pressure regulator and rotameter with needle valve. The carbon monoxide passes through a heated commercial "deoxo" unit as marketed by Engelhard Industries, Division, Engelhard Minerals and Chemicals Corp., Newark, N.J., to remove oxygen impurities. The nitrogen admixed with hydrogen pass through a similar "deoxo" unit before entering the reactor. Propylene is fed as a liquid to a preheater section or plenum chamber, where it is combined with the other feed gases and is vaporized prior to entering the reactor via the stainless steel filter element. The propylene feed rate is measured using rate-of-level drop in a tank containing liquid propylene using an armored rotameter with a needle valve to control the liquid propylene feed rate.

In operation, the catalyst is contained as a solution in the lower portion of the reactor tube and the reactant gases are sparged up through the solution (catalyst system) as bubbles emanating from the filter element. Product butyraldehyde is formed in the catalyst system where it accumulates and eventually is removed as a vapor by vapor/liquid equilibration with unreacted gases. This type of reactor is known as a vapor take-off or vapor stripped reactor. The hot gases are cooled upon leaving the reactor through said side port and the butyraldehyde product, along with some unreacted propylene, collects in a cooled high pressure separator connected by suitable conduit means to said side port. The noncondensed gases are let down to atmospheric pressure via a back pressure regulator which controls the reactor pressure. Additional butyraldehyde is condensed out of the atmospheric pressure gas stream by passing it through a series of three dry ice traps. Once an hour the contents of the high pressure separator and dry ice traps are collected and combined. The weight of butyraldehyde product obtained during the hour and its n/iso ratio are calculated using standard gas/liquid chromatographic techniques in combination with the crude weight of the product collected. In practice, approximately one hour is required for this bench unit to reach steady state production rates where catalyst activity and n/iso product ratio remain substantially constant.

A catalyst charge was prepared as in Example 1 using about 340 mg of tricyclohexylphosphine and rhodium 2-ethylhexanoate solution in Texanol solvent containing about 14.0 mg of rhodium as the metal in a total volume of 174 mL of Texanol solvent. This preparation was carried out under nitrogen and the catalyst solution charged to the bench unit reactor under argon. After sealing, the reactor was pressured to 200 psig with hydrogen, carbon monoxide, and nitrogen and heated to 125° C. by an external oil bath with said gases purging through the catalyst solution. The gas feed rates at STP were $H_2=CO=3.36$ liters per minute. Propylene feed was then started at 1.92 liters per minute as gas at STP. The run was carried out for a total of 5 hours at about 200 psig and 125° C. Reactor catalyst volume was kept at a standard operating level of 175 mL by pumping in Texanol solvent if level drop occurred as measured by a liquid level differential pressure cell attached to the reactor. The average butyraldehyde production rate for the last 4 hours of operation was 60.9 grams per hour, equivalent to a catalyst activity of 9.58 pounds of butyraldehyde per gram Rh-hour (lb HBu/g Rh-hr) with a n/iso ratio of 1.2/1.

EXAMPLE 3

Concentration and Recovery of Tricyclohexylphosphine - Rhodium Catalyst with Hexane Diluent and Methanol-Water Extractant This example demonstrates a preferred embodiment of the invention concentration/recovery process wherein the portion of the catalyst system was obtained as a side draw (807 mL) from the hydroformylation operation of Example 2 which had reached steady-state conditions. This portion was taken at a rate of about 0.008% of the reactor contents/hour and contained a trace of tricyclohexylphosphine and 7.4 grams per liter of tricyclohexylphosphine oxide. This portion was reduced in volume in a wiped film evaporator at 180° C. and 1 mm Hg to give 50 mL of catalyst system which was then admixed with 250 mL of hexane under a $N_2$ blanket. Tricyclohexylphosphine (1.5 grams) was added to stabilize the catalyst since there was very little free phosphine ligand present in the side draw. A mixture of methanol (240 mL) and water (60 mL) was added and the mixture stirred and heated to reflux for 2 hours. The mixture was cooled to room temperature and filtered to remove solids. The layers were separated, analyzed, and concentrated. The concentrate of the hexane layer was tested for hydroformylation activity and was found to have activity equivalent to the starting hydroformylation catalyst. The analysis of the catalyst solution is given in Table I.

TABLE I

| Layer | Volume, Liters | Metals, ppm Rh | Metals, ppm Fe | Tricyclo-hexyl-phosphine | Tricyclo-hexyl-phosphine Oxide |
|---|---|---|---|---|---|
| Start. Cat. | 0.807 | 345 | 40 | Trace | 5.97 grams |
| Hexane | 0.240 | 1,100 | 18 | 6.2 gm/l | 1.37 grams |
| $CH_3OH/H_2O$ | 0.250 | 7 | <0.1 | None | 4.60 grams |

EXAMPLE 4

Concentration and Recovery of Diphenylcyclohexylphosphine-Rhodium Catalyst with Hexane Diluent and Methanol-Water Extractant This example demonstrates that the initial volume reduction of the catalyst system portion (side draw) may be omitted, and that the invention is applicable to a variety of phosphine ligands, including e.g., diphenylcyclohexylphosphine.

A hydroformylation catalyst solution (50 mL) obtained from a hydroformylation generally carried out as described above, composed of high boilers (aldol condensation products) and butyraldehydes containing 35.9 mg of diphenylcyclohexylphosphine oxide, and 4.1 mg of rhodium was combined with 250 mL of hexane under nitrogen. Methanol (240 mL) and water (60 mL) were added and the mixture refluxed under $N_2$ for 2 hours. The mixture was cooled, the layers separated, and analyzed to give the data in Table II.

TABLE II

| Layer | Volume, Liters | Rh, mg | Phosphine, % | Phosphine Oxide, % |
|---|---|---|---|---|
| Hexane | 0.253 | 3.80 (93%) | 100 | 26 |
| Methanol/Water | 0.325 | 0.29 (7%) | 0 | 74 |

EXAMPLE 5

Concentration and Recovery of Tribenzylphosphine-Rhodium Catalyst and 2,2'-Bis(diphenylphosphinemethyl)-1,1'-biphenyl with Nonpolar Diluent and Aqueous Organic Extractant

Extraction Procedure

The specified volume of spent catalyst was optionally subjected to stripping and then diluted with the specified volume of nonpolar diluent. In this example, the stripping procedure, when used, consisted of heating the catalyst solution to 100° C. under a nitrogen purge until the desired concentrating effect had been achieved. The catalyst, diluted in the nonpolar diluent was then washed with the extractant at the specified temperature, the layers separated and the volumes of each layer measured. The nonpolar phase was titrated for organophosphine content. Both phases were analyzed by gas chromatographic methods for phosphine and phosphine oxides. Rhodium analysis were performed on both phases.

Dilution/extraction conditions are summarized in Table III, and rhodium/phosphine/phosphine oxide recoveries are summarized in Table IV.

TABLE III

Extraction Process Data

| Run No. | Starting Catalyst, (mL) | Concentration Factor | Phosphine Oxide Present* | Non-Polar Diluent (mL) | Extractant (mL) | Extraction Temp., °C. | Volume Non-Polar Phase, (mL) | Volume Polar Phase, (mL) |
|---|---|---|---|---|---|---|---|---|
| 1 | 200 | 0.3 | TBPO | Hexane (100) | 80% Methanol (100) | 25 | 125 | 115 |
| 2 | 200 | 0.5 | TBPO | 1-Hexene (100) | 80% Methanol (100) | 25 | 210 | 63 |
| 3 | 100 | 1 | BISBI-02 BISBI-0 | 1-Hexene (220) | 82% Methanol (320) | 25 | 384 | 222 |
| 4 | 100 | 1 | TBPO | Hexane (200) | 75% Diethylene Glycol (200) | 25 | 294 | 195 |
| 5 | 100 | 1 | TBPO | 1-Hexene (200) | 75% Ethylene Glycol (200) | 25 | 254 | 214 |
| 6 | 100 | 1 | TBPO | 1-Octene | 72% Ethylene | 65 | 250 | 350 |

TABLE III-continued

| | | | | Extraction Process Data | | | | |
|---|---|---|---|---|---|---|---|---|
| Run No. | Starting Catalyst, (mL) | Concentration Factor | Phosphine Oxide Present* | Non-Polar Diluent (mL) | Extractant (mL) | Extraction Temp., °C. | Volume Non-Polar Phase, (mL) | Volume Polar Phase, (mL) |
| | | | | (200) | Glycol (350) | | | |

*TBPO is tribenzylphosphine oxide
BISBI-0 and BISBI-02 are the mono and dioxides of 2,2'Bis(diphenylphosphinomethyl)-1,1'-biphenyl

TABLE IV

| Run No. | Phosphine Oxide in Spent Cat. | Phosphine Oxide in Extractant | Phosphine Oxide in Non-Polar | % Extraction of Phosphine Oxide | Rhodium in Spent Catalyst, mg | Rhodium in Extractant mg | Rhodium in Non-Polar Phase, mg | Rhodium Account | Phosphine in Spent Catalyst, gm | Phosphine in Non-Polar Phase, gm | Phosphine Account % |
|---|---|---|---|---|---|---|---|---|---|---|---|
| 1 | 4.05 | 2 | 2.05 | 49 | 21.2 | 0.15 | 21 | 99 | 1.26 | 0.97 | 77 |
| 2 | 6.51 | 1.03 | 5.48 | 15.8 | 31 | 0.5 | 30.45 | 99 | 1.51 | 1.3 | 86 |
| 3 | 0.40 BISBI-0 0.19 BISBI-02 | 0.08 | 0.40 BISBI-0 0.11 BISBI-02 | 14 | 17.5 | 0.5 | 12.7 | 73 | 1.11 | 1.14 | 100 |
| 4 | 1.11 | 0.4 | 0.71 | 36 | 8 | 0 | 8 | 100 | 0.59 | 0.43 | 73 |
| 5 | 3.06 | 2.23 | 0.83 | 73 | 18 | 0.2 | 18.2 | 100 | 0.5 | 0.33 | 66 |
| 6 | 5.31 | 1 | 4.31 | 81 | 17.3 | 0.1 | 16.5 | 96 | 0.56 | 0.24 | 43 |

These results demonstrate that the invention process is effective for the treatment of catalyst systems which employ a variety of phosphine moieties. In addition, a variety of nonpolar diluents and aqueous organic extractants are seen to be effective.

While the invention has been described in detail with particular reference to preferred embodiments thereof, it will be understood that variations and modifications can be effected within the spirit and scope of the invention.

That which is claimed is:

1. A process for recovering or concentrating active catalyst materials from a substantially homogeneous system comprising:
   (a) active catalyst materials which comprise
      (i) triorganophosphine-rhodium complexes, and
      (ii) free triorganophosphine;
   (b) oxidized triorganophosphine residues,
   (c) iron carboxylate salts,
   (d) pump oils, and
   (e) aldehydes and aldol condensation products thereof; said processing comprising:
   (1) admixing a portion of said homogeneous system with about 1 up to 100 volumes, relative to the volume of said portion of at least one nonpolar hydrophobic hydrocarbon diluent selected from the group consisting of saturated or unsaturated aliphatic hydrocarbon having in the range of 3 up to 20 carbon atoms and aromatic or hydrocarbyl-substituted aromatic hydrocarbons having in the range of 6 up to 22 carbon atoms to produce a diluted homogeneous system,
   (2) contacting said diluted homogeneous system with 0.1 up to 20 volumes, relative to the volume of said nonpolar hydrophobic solvent, of at least one aqueous polar hydrophilic organic solvent selected from the group consisting of:
   aliphatic carboxylic acids having in the range of 1 up to 3 carbon atoms,
   aliphatic alcohols having in the range of 1 up to 3 carbon atoms,
   acetonitrile,
   acetone,
   dimethylformamide,
   dimethylacetamide,
   methyl ethyl ketone,
   1,4-dioxane,
   polyols having in the range of 2 up to 6 carbon atoms,
   glycol ethers having in the range of 4 up to 12 carbon atoms,
   as well as mixtures of any two or more thereof, and allowing the nonpolar hydrophobic hydrocarbon solvent and the aqueous polar hydrophilic organic solvent to separate into layers, and thereafter
   (3) separating the hydrocarbon layer from the aqueous polar hydrophilic organic layer.

2. The process of claim 1 further comprising recovering concentrated active catalyst materials from said nonpolar hydrophobic solvent layer by removing said solvent therefrom.

3. The process of claim 1 wherein said nonpolar hydrophobic hydrocarbon diluent is selected from the group consisting of:
propane,
propylene,
butane,
butene,
pentane,
pentene,
hexane,
hexene,
heptane,
heptene,
octane,
octene,
kerosene,
mineral spirits,
petroleum ethers,
as well as a mixture of any two or more thereof.

4. The process of claim 1 wherein said contacting is carried out with agitation of the admixture for a period of from about 1 to about 20 hours at from about 20° C. to about 30° C.

5. The process of claim 1 wherein said contacting is carried out with agitation at reflux for a period of from about 10 minutes to about 4 hours.

6. The process of claim 1 wherein the layers produced in step (2) are filtered prior to carrying out the step (3).

7. The process of claim 1 wherein the portion of said homogeneous system subjected to admixing in accordance with step (1) is reduced to about 1/5 to about 1/50 of its initial volume prior to further treatment thereof, the volumetric ratio of nonpolar hydrophobic solvent to said portion is from about 1 to about 100, and the volumetric ratio of said aqueous polar hydrophilic solvent to said diluent is from about 0.1 to about 20.

8. The process of claim 1 wherein the portion of said homogeneous system subjected to admixing in accordance with step (1) is reduced to about 1/15 to about 1/25 of its initial volume prior to further treatment thereof, the volumetric ratio of nonpolar hydrophobic solvent to said portion is from about 1.0 to about 10, and the volumetric ratio of said aqueous polar hydrophilic solvent to said diluent is from about 0.5 to about 3.0.

9. The process of claim 1 wherein the portion of said homogeneous system subjected to admixing in accordance with step (1) is reduced to about 1/15 to about 1/25 of its initial volume prior to further treatment thereof, the volumetric ratio of nonpolar hydrophobic solvent to said portion is from about 1 to about 7.0, and the volumetric ratio of said aqueous polar hydrophilic solvent to said diluent is from about 0.8 to about 1.5.

10. A process for recovering or concentrating active catalyst materials from a substantially homogeneous system comprising:
(a) active catalyst materials which comprise
  (i) triorganophosphine-rhodium complexes, and
  (ii) free triorganophosphine;
(b) oxidized triorganophosphine residues,
(c) iron carboxylate salts,
(d) pump oils, and
(e) aldehydes and aldol condensation products thereof; wherein the substantially homogeneous system is the reaction mixture resulting from a hydroformylation process comprising contacting at least one olefin having from 2 to about 20 carbon atoms or other unsaturated organic compounds in a reaction zone at a temperature of from about 20° C. to about 250° C. and a pressure of from about 50 psig to about 800 psig with hydrogen, carbon monoxide, and a catalyst comprising rhodium in chemical complex with one or more ligands of the formula $P(R)_3$ or bidentate phosphorus moieties having the formula $PR_2-L-PR_2$ wherein each R is independently a hydrocarbyl moiety having from 1 up to 20 carbon atoms, wherein each of these radicals can be substituted with 1-3 hydrocarbyl radicals, wherein any of the above hydrocarbyl radicals can be substituted with 1-3 groups selected from alkoxy, aryloxy, cycloalkoxy, carboxyesters, carboxy, alkanoyl, aroyl, hydroxy, alkoxyalkoxy, alkoxyalkyl, or acyloxy, wherein any of the above aryl radicals can be substituted with 1-3 of the above groups or halogen or cyano; and wherein L is an alkylene, alkenylene, or arylene moiety having in the range of 1-20 carbon atoms, and can be substituted as is described for R;
said process comprising:
(1) admixing a portion of said homogeneous system with about 1 up to 100 volumes, relative to the volume of said portion, of at least one nonpolar hydrophobic hydrocarbon diluent selected from the group consisting of saturated or unsaturated aliphatic hydrocarbon having in the range of 3 up to 20 carbon atoms and aromatic or hydrocarbyl-substituted aromatic hydrocarbons having in the range of 6 up to 22 carbon atoms to produce a diluted homogeneous system,
(2) contacting said diluted homogeneous system with 0.1 up to 20 volumes, relative to the volume of said nonpolar hydrophobic solvent, of at least one aqueous polar hydrophilic organic solvent selected from the group consisting of:
aliphatic carboxylic acids having in the range of 1 up to 3 carbon atoms,
aliphatic alcohols having in the range of 1 up to 3 carbon atoms,
acetonitrile,
acetone,
dimethylformamide,
dimethylacetamide,
methyl ethyl ketone,
1,4-dioxane,
polyols having in the range of 2 up to 6 carbon atoms,
glycol ethers having in the range of 4 up to 12 carbon atoms,
as well as mixtures of any two or more thereof, and allowing the nonpolar hydrophobic hydrocarbon solvent and the aqueous polar hydrophilic organic solvent to separate into layers, and thereafter
(3) separating the hydrocarbon layer from the aqueous polar hydrophilic organic layer.

11. The hydroformylation process according to claim 10 wherein said reaction zone is operated at temperatures between about 80° C. and 150° C. and at pressures between about 100 psig and 400 psig, and the molar ratio of ligand to rhodium is from about 0.5 to about 200.

12. The hydroformylation process according to claim 11 wherein the molar ratio of said hydrogen to carbon monoxide is at least 0.5, and the total moles of hydrogen and carbon monoxide are present in said reaction zone in the ratio range of from 0.5 to about 20 with respect to moles of said olefin.

13. The hydroformylation process according to claim 12 wherein said olefin is selected from one or more of ethylene, propylene, 2-methylpropylene, 2-butene, 1-butene, 2-methyl-1-butene, 1-pentene, 1-hexene, 1-heptene and 1-octene.

14. The hydroformylation process according to claim 13 wherein said rhodium is present in said reaction zone in an amount between about $1 \times 10^{-6}$ to about $1 \times 10^{-1}$ moles per mole of said olefin present in said reaction zone.

15. The process of claim 10 wherein said ligand is selected from phenyl, alkyl, benzyl, cyclohexyl, cyclohexylalkyl and mixtures thereof.

16. The process of claim 15 wherein the olefin is propylene.

17. The process of claim 16 wherein the molar ratio of ligand to rhodium is from about 2 to about 10.

18. The process of claim 17 wherein the molar ratio of ligand to rhodium is from about 2.3 to about 4.

* * * * *